United States Patent [19]

Burr

[11] Patent Number: 4,998,954
[45] Date of Patent: Mar. 12, 1991

[54] ISOKINETIC PROBE AND PRESSURE REDUCTION ASSEMBLY

[75] Inventor: William J. Burr, Newfane, N.Y.

[73] Assignee: Union Carbide Industrial Gases Technology Corporation, Danbury, Conn.

[21] Appl. No.: 467,568

[22] Filed: Jan. 19, 1990

[51] Int. Cl.⁵ .............................................. G01N 1/00
[52] U.S. Cl. ................................. 73/863.58; 73/863.86
[58] Field of Search ................. 73/28, 863.51, 863.54, 73/863.57, 863.58, 863.61, 863.81, 863.82, 863.85, 863.86, 864.73, 864.81, 866.5, 863.58, 863.86

[56] References Cited

U.S. PATENT DOCUMENTS

| 2,452,224 | 10/1948 | Collet, Jr. | 73/863.58 |
| 2,872,810 | 2/1959 | Shaffer | 73/213 |
| 3,252,323 | 5/1966 | Torgeson | 73/170 |
| 3,473,388 | 10/1969 | Lynn | 73/422 |
| 3,699,814 | 10/1972 | Kaufman | 73/864.34 |
| 4,060,001 | 11/1977 | Archerd | 73/421.5 R |
| 4,198,860 | 4/1980 | King | 73/195 |
| 4,413,533 | 11/1983 | Diesel | 73/863.58 |
| 4,456,014 | 6/1984 | Buck et al. | 73/863.86 |
| 4,631,961 | 12/1986 | Yohe et al. | 73/863.85 |
| 4,651,572 | 3/1987 | Albertz et al. | 73/861.63 |
| 4,742,717 | 5/1988 | Ichino | 73/866.5 |
| 4,854,180 | 8/1989 | Mauleon et al. | 73/863.86 |

FOREIGN PATENT DOCUMENTS 471307  5/1975  U.S.S.R. .............................. 73/863.51

Primary Examiner—Robert Raevis
Attorney, Agent, or Firm—Stanley Ktorides

[57] ABSTRACT

A gas sampling apparatus wherein a retractable isokinetic probe is insertable into a gas flow line through aligned guide tubes and a gas sample is isokinetically conveyed to a converging-diverging nozzle where its pressure is reduced by a controlled shock wave.

10 Claims, 2 Drawing Sheets

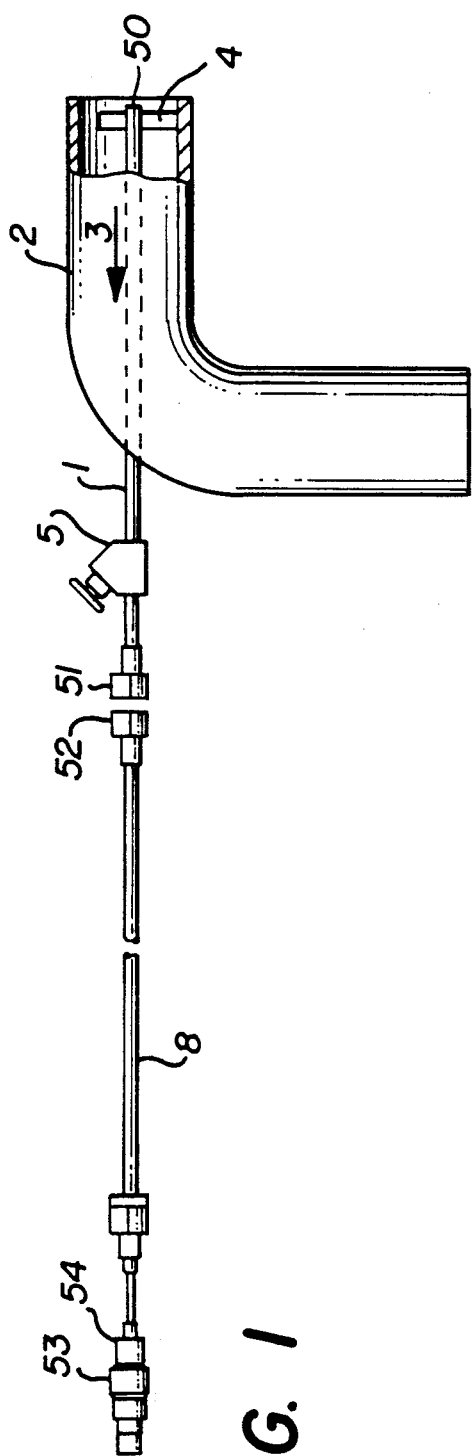
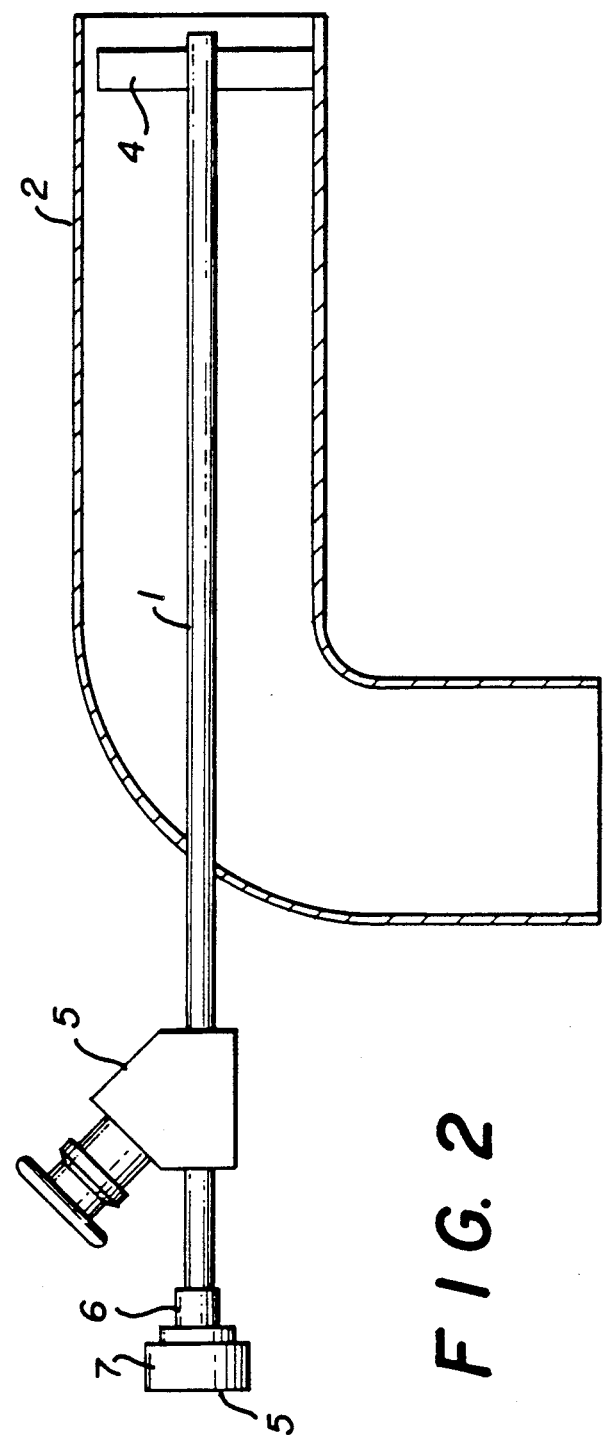
FIG. 1
FIG. 2

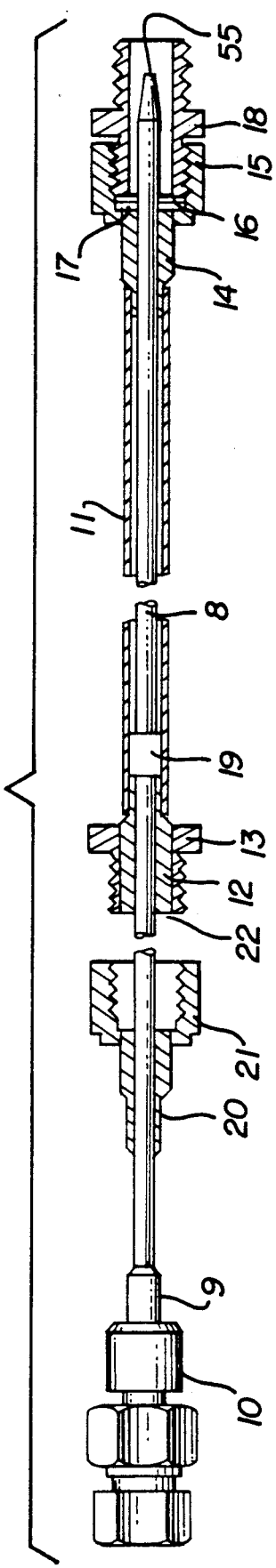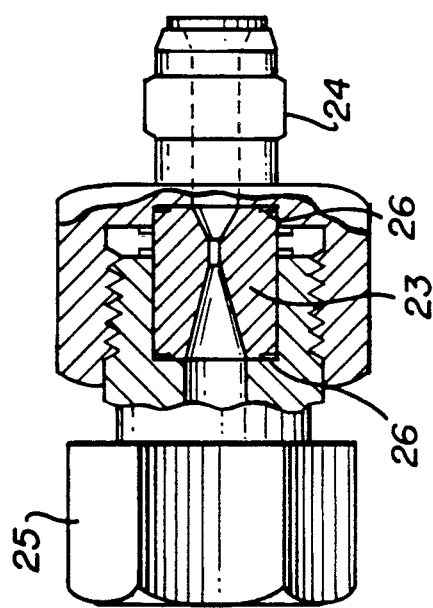

ISOKINETIC PROBE AND PRESSURE REDUCTION ASSEMBLY

TECHNICAL FIELD

This invention relates generally to the obtaining of a gas sample from a flowing gas stream, and more specifically to the obtaining of such a gas sample for the purpose of determining the particulate content of the gas stream.

BACKGROUND ART

The electronics industry employs gases, such as nitrogen, in manufacturing operations, such as in the manufacture of very large scale integrated circuits. Increasingly the cleanliness or purity requirements of such gases are becoming more stringent. In particular, the particulate content of such gases is critical to the quality of the product produced by such manufacturing operations.

In order to maintain good quality control over the manufacturing process, the particulate content of the gas must be monitored and measured. Since the gas is supplied to the manufacturing operation at an elevated pressure and since the particulate measuring equipment generally operates at about atmospheric pressure, the pressure of the gas sample must be reduced, often by a factor of ten or more, prior to passage to a particulate counter. This pressure reduction is generally done through a valve or critical orifice usually containing moving or rubbing parts. This causes the generation of significant quantities of particulates thus reducing the accuracy of the measurement. Since the particulate content of the gas is of the order of only a few particles per cubic foot, it can be seen that even minor particulate generation due to the sampling device would have a detrimental effect on the accuracy of the particulate measurement.

Moreover, conventional gas sampling devices generally contain bends or other potential for dead spaces which trap and remove particles from the sample gas, thus further compromising the integrity of the particulate measurement.

In addition, with conventional sample collection systems, the product gas flow must be stopped and the product line depressurized to allow the sample collection device to be connected. This not only causes production delays but also exposes the product gas line to contamination from the outside atmosphere.

Accordingly, it is an object of this invention to provide a gas sampling device which can be inserted into a gas process stream without disturbing the operation of the gas supply or causing contamination of the gas supply system.

It is another object of this invention to provide a gas sampling device which can reduce the pressure of a gas sample without altering the particulate content of the sample.

SUMMARY OF THE INVENTION

The above and other objects which will become apparent to one skilled in the art upon a reading of this disclosure are attained by the present invention one aspect of which is:

An isokinetic probe and pressure reduction assembly comprising:

(A) a probe guide tube having input and output ends, said probe guide tube being insertable within and in-line with a gas flow;

(B) an isolation valve on the probe guide tube between the input and output ends of the probe guide tube;

(C) a support guide tube having input and output ends, the input end of the support guide tube being matable with the output end of the probe guide tube;

(D) a moveable isokinetic probe having input and output ends, capable of movement within the support guide tube and the probe guide tube; and (E) a converging-diverging nozzle assembly matable with the output end of the isokinetic probe for flow communication with the isokinetic probe.

Another aspect of the invention is:

A method for taking a gas sample from a process gas flow line comprising:

(A) providing a gas flow line having installed thereon an isokinetic probe and pressure reduction assembly comprising a probe guide tube having input and output ends installed within and in-line with gas flowing within the gas flow line; an isolation valve on the probe guide tube between the input and output ends of the probe guide tube; a support guide tube having input and output ends, the input end of the support guide tube being mated to the output end of the probe guide tube; a moveable isokinetic probe having input and output ends capable of movement within the support guide tube and the probe guide tube; and a converging-diverging nozzle assembly mated with the output end of the isokinetic probe for flow communication with the isokinetic probe;

(B) passing a gas through the gas flow line;

(C) opening the isolation valve and moving the isokinetic probe into the gas flow line;

(D) passing gas isokinetically from the gas flow line into the isokinetic probe;

(E) retracting the isokinetic probe from the gas flow line and closing the isolation valve; and (F) maintaining the flow of gas through the gas flow line during each of steps (C), (D) and (E).

As used herein, the term "isolation valve" means a valve which is used to shut off and isolate a gas flow from the outside atmosphere when the isokinetic probe is not inserted into the gas flow.

As used herein, the term "isokinetic probe" means a device comprising a small diameter tube insertable into a gas flow to collect a sample of gas from the gas flow under isokinetic conditions. Isokinetic conditions mean that the probe orientation and flow path are parallel to the gas flow from which the sample is taken and that the velocity and hence the kinetic energy of the gas entering the probe is equal to the velocity and hence the kinetic energy of the gas flow.

As used herein, the term "critical orifice" means a plate positioned across a flow passage through which a sharp edge hole has been cut, wherein the area of the hole is sufficiently small that gas flowing through the hole accelerates to critical, i.e. sonic, velocity.

As used herein, the term "high hardness" means a material with a Brinell hardness number of at least 500.

BRIEF DESCRIPTION OF THE DRAWINGS

FIG. 1 is an overall view of the isokinetic probe and pressure reduction assembly of this invention.

FIG. 2 is a detailed view partly in cross-section of the probe guide tube subassembly and the isolation valve of the assembly of this invention.

FIG. 3 is a detailed cross-sectional view of the support guide tube subassembly and the moveable isokinetic of the assembly of this invention.

FIG. 4 is a cross-sectional view of the converging-diverging nozzle of the assembly of this invention.

DETAILED DESCRIPTION

The isokinetic probe and pressure reduction assembly of this invention will be described in detail with reference to the Drawings.

Referring now to FIG. 1, the probe guide tube subassembly comprises probe guide tube 1 and the connector fittings on the output end of probe guide tube 1. Probe guide tube 1 is inserted within gas flow line 2, preferably at a bend or an elbow, such as is shown in FIG. 1, or, for example, a T or L shaped joint, so as to be in line with gas flow within line 2 as represented by arrow 3. If desired, probe guide 1 may be supported within gas flow line 2 by support 4. Isolation valve 5 is on probe guide tube 1 between the input end 50 and output end 51 of probe guide tube 1. Support guide tube 11 connects with probe guide 1 by mating input end 52 of support guide tube 11 with output end 51. Within support guide tube 11, as will be more fully described later, is moveable isokinetic probe 8. Converging-diverging nozzle assembly 53 matingly connects with output end 54 of isokinetic probe 8.

Referring now to FIG. 2, there is shown more clearly isolation valve 5. Preferably isolation valve 5 is a Y-configuration valve with a bellows seal on the valve stem. In the closed position the isolation valve isolates or closes off probe guide tube 1 and hence the gas flow in line 2 from the external atmosphere. When isolation valve 5 is opened the poppet and stem pull fully out of probe guide tube 1 creating a straight passage through which isokinetic probe 8 can be inserted into the gas flow. After isokinetic probe 8 has been positioned past the isolation valve and into the gas flow, these valve generated particles, if any, cannot enter the isokinetic probe. When in place, the isokinetic probe seals the isolation valve and the gas flow from the external atmosphere. The region around and within isolation valve 5 is consequently a non-flow region and hence no particles can flow from that region into the gas flow or into the isokinetic probe.

At output end 51 on probe guide tube 1 there is connector fitting 6 and nut 7 which serve to mate the probe guide subassembly to the support guide subassembly. The probe guide subassembly creates a straight passage through which the sealed isokinetic probe can be inserted in the gas flow stream. When the isokinetic probe is not inserted within the gas flow stream, isolation valve 5 is closed thus sealing the gas flow stream.

Referring now to FIG. 3, there is illustrated the support guide subassembly which herein comprises isokinetic probe 8 having a capture probe tip 55 on its upstream or input end and a nozzle connector fitting 9 and nut 10 on its output end. Support guide tube 11 has fitting 12 and nut 13 at its downstream or output end, and has fitting 14 and nut 15 at its upstream or input end. Fitting 14 is machined to accept energized Teflon ™ spring loaded seal 16 and gasket 17. Gasket 17 is a blank gasket which is drilled to pass isokinetic probe 8 and act as a retainer for seal 16. Retainer gasket 17 holds seal 16 within fitting 14 as isokinetic probe 8 is inserted into or withdrawn from gas flow line 2. Retainer gasket 17 is held in place by double union 18 installed into upstream nut 15. The other end of double union 18 is used for mounting the support guide subassembly to the probe guide subassembly.

Isokinetic probe tube 8 from tip 55 to nozzle connector fitting 9 is generally over twice as long as support tube 11 from connector fitting 14 to connector fitting 12, and slides back and forth within support tube 11, restrained by slide stop 19 which can move only between fitting 14, in the fully inserted position, and fitting 12, in the fully retracted position.

Support guide tube 11 is fixed to fittings 12 and 14 to form an integral unit to hold isokinetic probe 8. Slide stop plug 19 is fixed to isokinetic probe tube 8 and permits isokinetic probe 8 to slide only the distance between fittings 12 and 14. This serves to prevent isokinetic probe 8 from being blown out of the probe guide subassembly by the force of the gas flow.

Fitting 20 and nut 21 are connected to isokinetic probe 8 and act to secure isokinetic probe 8 to support guide tube 11 after isokinetic probe 8 has been inserted into the gas flow line. Gasket retainer assembly 22 completes the seal of isokinetic probe 8 to the probe guide subassembly.

Referring now to FIG. 4 the convergingdiverging nozzle assembly comprises nozzle piece 23 which is sealed into upstream holder piece 24 and into downstream holder piece 25 by stainless steel o-rings 26. Nozzle piece 23 is made of high hardened material which resists abrasion by high velocity sonic gas and therefore does not shed particles. The smooth flow path through the converging-diverging nozzle assembly eliminates sharp edges which would erode in a high velocity gas stream and generate contaminating particles. In addition, the smooth flow path eliminates dead volumes or sharp flow channel variations which would trap particles or create highly turbulent regions which might alter the particulate content of the gas sample.

The high pressure drop created by nozzle piece 23 causes the velocity of the gas sample to become sonic and creates the sonic flow control. The gas flow starts to go supersonic in the downstream divergent portion of the nozzle and shocks down from supersonic to subsonic to create the pressure reduction function of the invention. The smooth flow path causes this pressure reduction to occur with minimum turbulence or flow disturbance over sharp edges which would occur with conventional critical flow orifices.

The gas velocity accelerates to sonic velocity at the throat of the nozzle, then continues to accelerate to supersonic velocity in the divergent portion of the nozzle. The pressure drop across the nozzle is sufficient to create the requisite gas acceleration. Perferably the pressure ratio across the nozzle exceeds 2.0. The supersonic flow in the divergent portion of the nozzle then suddenly drops to subsonic across a very sharp, thin shock wave. This shock wave will remain in the divergent portion of the nozzle since the expansion area ratio is great enough, preferably greater than about 60, most preferably about 68, and the pressure ratio is large enough but does not exceed the maximum size for the respective nozzle size, generally about 40.0. If the nozzle were short with a low expansion area ratio and terminated in a sudden area expansion, the shock wave would occur in the free jet stream downstream, outside of the nozzle. This would produce highly turbulent flow with back flow recirculation regions which will act to generate or entrap particles and hence bias the particulate content of the sample gas.

For operation, the probe guide subassembly comprising the probe guide tube and the isolation valve is installed on a process line such as is shown in FIGS. 1 and 2. Once this subassembly is in place the isokinetic probe and the converging-diverging nozzle assembly can be employed whenever desired to collect a gas sample without requiring a shut down of the gas flow. Preferably the probe guide subassembly is installed on the process line as part of the fabrication of the process line.

During normal operation of the process line, isolation valve 5 is closed and fitting 6 is capped. When the taking of a gas sample is desired, the cap on fitting 6 is removed. Isokinetic probe 8 is pulled back into support guide tube 11 and the support guide and nozzle subassemblies are connected to the probe guide subassembly by mating double union 18 to connector fitting 6. A gasket is used between the two mating faces and the connection is tightened to establish a gas seal between the probe guide subassembly and the support guide subassembly.

Isolation valve 5 is opened and isokinetic probe 8 is pushed through the probe guide and into the gas flow. When support guide tube 11 is connected to probe guide tube 1, they form a combined outer sheath tube through which isokinetic probe 8 passes as it is pushed from its withdrawn, nested position back in support guide 11, up through to its inserted position, penetrating into the gas flow line fully through and beyond probe guide tube 1. Isokinetic probe 8 is long enough that in its inserted position it extends from within the gas flow line several inches beyond the end of probe guide tube 1, back through probe guide tube 1 and support guide tube 11 to the insertion locking nuts 21 and 13, and beyond to the nozzle assembly connection fitting 9.

Isokinetic probe 8 is secured into position by mating nut 13 on the downstream end of support guide tube 11 with nut 21 which is fixed to isokinetic probe 8. During this insertion operation sliding seal 16 maintains the seal between the process gas stream and the outside atmosphere. Once isokinetic probe 8 has been secured into position, the outlet of the converging-diverging nozzle assembly can be connected to a particulate counting instrument.

When the testing is completed, the isokinetic probe is removed and the gas flow sealed by isolation valve 5 by reversing the process described above.

Isokinetic sample capture means that the velocity of the sample gas entering the probe is equal to the velocity of the gas in the main gas flow stream so that both the sample gas and the main gas flows are at the same fluid kinetic conditions. When this happens, all of the particles which existed in the sample gas while it was in the process gas flow stream are captured by the probe and a representative gas-particle sample is captured. If the flow is not isokinetic, the sample gas and the surrounding gas undergo rapid direction changes around the probe tip, convergent in the case of super-isokinetic capture and divergent in the case of sub-isokinetic capture. Since the particles have a much higher unit mass than does the gas, they cannot make the rapid flow direction changes. Under super-isokinetic capture conditions, particles which are in the sample gas about to be captured cannot follow the gas into the probe and pass by outside the probe. Under subisokinetic capture conditions, particles which are in the gas outside of the sample gas to be captured cannot follow this external flow as it deflects around the probe, and enter into the probe, adding to the particles in the sample gas captured. Under these non-isokinetic conditions the number of particulates captured by the probe is not the same as existed in the sample of the gas prior to capture by the probe and the particulate level in the sample gas captured by the probe is biased away from the true gas stream value.

The assembly of the invention was employed to capture gas samples from a gas flow flowing at a steady state at a pressure of 70 pounds per square inch gauge (psig) and a flowrate of 110 standard cubic feet per hour (scfh). The average particulate count for these samples was 2.92 per cubic foot. For comparative purposes similar sampling was carried out except that a conventional valve-based assembly was employed. The average particulate count for these comparative samples was 11.71 per cubic foot.

The assembly of this invention was employed to capture gas samples from a gas flow flowing with a pulsed flow at pressures from 70 to 80 and back to 70 psig and at a flowrate between 110 and 125 scfh. The average particulate count for these samples was 2.42 per cubic foot. For comparative purposes similar sampling was carried out except that a conventional valve-based assembly was employed. The average particulate count for these comparative samples was 23.80 per cubic foot.

Now by the use of the isokinetic probe and pressure reduction assembly of this invention one can more effectively and accurately obtain a gas sample from a gas process flow line. The elements of the invention are oriented straight or in-line thus eliminating bends which might cause stagnation regions, turbulent recirculation pockets or sharp flow area changes which could trap particulates and alter the particulate content of the gas sample. There are no sharp edges such as would occur at a critical orifice which would serve to generate particulates. The gas sample is withdrawn from the gas flow isokinetically, at a velocity equal to the gas flow velocity, thus preserving the particulate content of the gas sample. Precise stable control of the gas sample flow rate is maintained because of the fixed and unchanging character of the converging-diverging nozzle throat. Thus there are no area changes which might occur as a valve seat changes setting as a result of vibration or mechanical creep of the various mating pieces of a valve. The converging diverging nozzle passage effectively contains the pressure reducing shock wave associated with flow pressure reduction. The shock wave in a conventional free jet supersonic flow creates turbulence which could scrub walls and create backflow recirculations which would trap particulates and hence alter the accuracy of the particulate level of the gas sample. The isokinetic probe can be put into position and then retracted after a sample is taken without shutting down the gas flow through the line or subjecting the gas flow line to contamination from the outside atmosphere.

Although the isokinetic probe and pressure reduction assembly of this invention has been described in detail with reference to one particular preferred embodiment as illustrated in the Drawings, those skilled in the art will recognize that there are other embodiments of the invention within the spirit and the scope of the claims.

I claim:

1. An isokinetic probe and pressure reduction assembly comprising:

(A) a probe guide tube having input and output ends, said probe guide tube being insertable within and in-line with a gas flow line;

(B) an isolation valve on the probe guide tube between the input and output ends of the probe guide tube;

(C) a support guide tube having input and output ends, the input end of the support guide tube being matable with the output end of the probe guide tube;

(D) a moveable isokinetic probe having input and output ends, capable of movement within the support guide tube and the probe guide tube; and (E) a converging-diverging nozzle assembly matable with the output end of the isokinetic probe for flow communication with the isokinetic probe.

2. The assembly of claim 1 wherein the probe guide tube, support guide tube, isokinetic probe, and converging-diverging nozzle assembly are aligned in a straight line.

3. The assembly of claim 1 further comprising a sliding seal between the support guide tube and the isokinetic probe.

4. The assembly of claim 1 wherein the surface of the converging-diverging nozzle assembly has a high hardness.

5. The assembly of claim 1 installed on a process gas flow line.

6. The assembly of claim 5 wherein the installation is at a bend in the process gas flow line.

7. The assembly of claim 5 wherein the process gas flow line is in operation with gas flowing through the line.

8. The assembly of claim 7 wherein the isokinetic probe is insertable into the process gas flow line and retractable from the process gas flow line without stopping the gas flowing through the line.

9. The assembly of claim 1 further comprising spaced fittings fixed to the support guide tube and a slide stop fixed to the isokinetic probe between the spaced fittings so as to restrain the movement of the isokinetic probe by the spaced fittings.

10. A method for taking a gas sample from a process gas flow line comprising:

(A) providing a gas flow line having installed thereon an isokinetic probe and pressure reduction assembly comprising a probe guide tube having input and output ends installed within and in-line with gas flowing within the gas flow line; an isolation valve on the probe guide tube between the input and output ends of the probe guide tube; a support guide tube having input and output ends, the input end of the support guide tube being mated to the output end of the probe guide tube; a moveable isokinetic probe having input and output ends capable of movement within the support guide tube and the probe guide tube; and a converging-diverging nozzle assembly mated with the output end of the isokinetic probe for flow communication with the isokinetic probe;

(B) passing a gas through the gas flow line;

(C) opening the isolation valve and moving the isokinetic probe into the gas flow line;

(D) passing gas isokinetically from the gas flow line into the isokinetic probe;

(E) retracting the isokinetic probe from the gas flow line and closing the isolation valve; and (F) maintaining the flow of gas through the gas flow line during each of steps (C), (D) and (E).

* * * * *

UNITED STATES PATENT AND TRADEMARK OFFICE
CERTIFICATE OF CORRECTION

PATENT NO.  :  4,998,954
DATED       :  March 12, 1991
INVENTOR(S) :  John W. Burr It is certified that error appears in the above-identified patent and that said Letters Patent is hereby corrected as shown below:

On the Title Page, in item 75, name of inventor, delete "William J. Burr" and insert therefor --John W. Burr--.

Signed and Sealed this

Eighteenth Day of August, 1992

Attest:

DOUGLAS B. COMER

*Attesting Officer*   *Acting Commissioner of Patents and Trademarks*